(12) United States Patent
Hilbig et al.

(10) Patent No.: US 11,596,761 B2
(45) Date of Patent: Mar. 7, 2023

(54) SYSTEM FOR HUMIDIFICATION OF A PRESSURIZED FLOW OF BREATHABLE GAS DELIVERED TO A PATIENT

(71) Applicant: KONINKLIJKE PHILIPS N.V., Eindhoven (NL)

(72) Inventors: Rainer Hilbig, Aachen (DE); Pascal De Graaf, Eindhoven (NL); Marcel Mulder, Eindhoven (NL); Achim Gerhard Rolf Koerber, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 319 days.

(21) Appl. No.: 16/623,428

(22) PCT Filed: Jun. 20, 2018

(86) PCT No.: PCT/EP2018/066332
§ 371 (c)(1),
(2) Date: Dec. 17, 2019

(87) PCT Pub. No.: WO2019/002033
PCT Pub. Date: Jan. 3, 2019

(65) Prior Publication Data
US 2020/0121886 A1   Apr. 23, 2020

(30) Foreign Application Priority Data
Jun. 28, 2017 (EP) .................................... 17178370

(51) Int. Cl.
*A61M 16/16* (2006.01)
*A61M 16/08* (2006.01)
*A61M 15/00* (2006.01)

(52) U.S. Cl.
CPC ........ *A61M 16/16* (2013.01); *A61M 15/0085* (2013.01); *A61M 16/0833* (2014.02); *A61M 2205/50* (2013.01); *A61M 2205/8206* (2013.01)

(58) Field of Classification Search
CPC .......... A61M 16/0833; A61M 16/0816; A61M 16/16; A61M 11/005; A61M 15/0085; A61M 16/142
See application file for complete search history.

(56) References Cited

U.S. PATENT DOCUMENTS

| 5,349,946 A | 9/1994 | McComb |
| 6,530,370 B1 | 3/2003 | Heinonen |

(Continued)

FOREIGN PATENT DOCUMENTS

JP     2005058709 A     3/2005

OTHER PUBLICATIONS

International Search Report—PCT/EP2018/066332 filed Jun. 20, 2018.

(Continued)

*Primary Examiner* — Joseph D. Boecker
*Assistant Examiner* — Thomas W Greig
(74) *Attorney, Agent, or Firm* — Daniel H. Brean; Andrew M. Gabriel

(57) ABSTRACT

The present invention provides a system (10) for humidification of a pressurized flow of breathable gas delivered to a patient, the system comprising; a ventilator (12) for generating a pressurized flow of breathable gas; a patient circuit (14) in fluid communication with the ventilator and connectable to the respiratory system of a patient; and an aerosol generator (18). The patient circuit defines an internal space (26) for transporting the flow of breathable gas which internal space accommodates the outflow opening (20) of (Continued)

the aerosol generator. This enables to prevent so-called rainout and a relatively light weight portable system. The invention also relates to an insert (30) that is connectable to the patient circuit and that accommodates the aerosol generator.

17 Claims, 3 Drawing Sheets

(56) References Cited

U.S. PATENT DOCUMENTS

| | | | |
|---|---|---|---|
| 6,598,602 B1 | 7/2003 | Sjoeholm | |
| 8,544,462 B2* | 10/2013 | Papania | A61M 15/0033 |
| | | | 128/200.16 |
| 8,603,439 B2 | 12/2013 | Montgomery | |
| 8,720,435 B2 | 5/2014 | Gallem et al. | |
| 8,985,100 B2* | 3/2015 | Minocchieri | A61M 16/142 |
| | | | 128/203.12 |
| 2008/0264412 A1* | 10/2008 | Meyer | A61M 15/009 |
| | | | 128/200.22 |
| 2009/0235925 A1* | 9/2009 | Power | A61M 16/16 |
| | | | 128/200.14 |
| 2010/0083968 A1 | 4/2010 | Cipollone et al. | |
| 2011/0146670 A1* | 6/2011 | Gallem | A61M 15/0036 |
| | | | 128/200.14 |
| 2011/0247616 A1* | 10/2011 | Von Hollen | A61M 16/0816 |
| | | | 128/203.12 |
| 2014/0182583 A1 | 7/2014 | Allum et al. | |
| 2015/0174344 A1* | 6/2015 | Minocchieri | A61M 16/108 |
| | | | 128/200.23 |
| 2016/0279351 A1 | 9/2016 | Gallem et al. | |
| 2017/0143931 A1 | 5/2017 | Ching et al. | |
| 2017/0368282 A1* | 12/2017 | Knoch | A61M 15/00 |
| 2019/0314598 A1 | 10/2019 | Hilbig et al. | |

OTHER PUBLICATIONS

Molloy, K. et al., "Hypertonic saline in treatment of pulmonary disease in cystic fibrosis." The Scientific World Journal, 2012: 465230, 2012. doi: 10.1100/2012/465230.

Valderramas, S.R. et al., Effectiveness and safety of hypertonic saline inhalation combined with exercise training in patients with chronic obstructive pulmonary disease: a randomized trial. Respiratory care, 54 (3): 327-333, 2009.

* cited by examiner

SYSTEM FOR HUMIDIFICATION OF A PRESSURIZED FLOW OF BREATHABLE GAS DELIVERED TO A PATIENT

CROSS-REFERENCE TO PRIOR APPLICATIONS

This application claims the priority benefit under 35 U.S.C. § 371 of International Patent Application No. PCT/EP2018/066332, filed on Jun. 20, 2018, which claims the priority benefit of European Patent Application No. 17178370.7, filed on Jun. 28, 2017, the contents of which are herein incorporated by reference.

FIELD OF THE INVENTION

The present invention relates to a system for humidification of a pressurized flow of breathable gas delivered to a patient. The invention further relates to an insert for use in such a system

BACKGROUND OF THE INVENTION

Patients with invasive ventilation delivered for example through a patient's trachea experience the situation that if dry ventilated air is delivered to them via a ventilator, the airways are drying out. Drying out of the upper airways due to inhalation of dry air over some period, is uncomfortable for the patient and can have a severe health impact after longer exposure. Inhalation of dry air over a longer period results in a drying of mucus in the upper airways, causing it to become very viscous, impeding mucus removal from the patient's airway. Excess mucus in the upper airways negatively effects the breathing of the patients and thus their quality of life, and if not removed poses a risk of inflammations. To support patients with non-invasive ventilation, e.g. severe chronic obstructive pulmonary disease (COPD) patients or patients with neuromuscular disorders, next to the ventilator a humidifier is supplied that humidifies the ventilated air.

US20090235925 discloses a system for humidification of a pressurized flow of breathable gas delivered to a patient having a ventilator, a patient circuit and an aerosol generator that is connected to the patient circuit by means of a connector. Such systems for humidification of a pressurized flow of breathable gas delivered to a patient of this general type may, however, be further improved.

SUMMARY OF THE INVENTION

The invention is defined by the claims.

According to examples in accordance with an aspect of the invention, there is provided a system for humidification of a pressurized flow of breathable gas delivered to a patient, in particular a system which can be used without the risk of liquid water getting into the patient's airways (rainout).

Towards this end, a first aspect of the invention provides a system for humidification of a pressurized flow of breathable gas delivered to a subject, the system comprising:

a ventilator for generating a pressurized flow of breathable gas;

a patient circuit in fluid communication with the ventilator and connectable to the respiratory system of a patient, the patient circuit defining an internal space for transportation of the breathable gas;

an aerosol generator for providing an aerosol of liquid, the aerosol generator having an outflow opening; wherein the outflow opening aerosol generator is provided within the internal space for entrainment of the aerosol of liquid.

The internal space of the patient circuit is used to transport the breathable gas from the ventilator to the connection with the respiratory system of a patient. Providing the outflow opening of the aerosol generator within the internal space enables a direct entrainment of the aerosol in the flow of breathable gas and with that prevents rain out, or at least reduces the chance to rainout. The aerosol generator can be positioned closer to the patient which further reduces the chance for condensation and thus rain out to occur. The system allows for an optimal mixing of the aerosolized liquid with the breathable gas. In an arrangement the outflow opening of the aerosol generator debouches in the open space of the patient circuit.

In an embodiment, the system further comprises an insert that is connectable to the patient circuit and that accommodates the aerosol generator. This enables an easy and straightforward way of mounting the aerosol generator. It even allows to easily chance between a regular ventilating system and a humidification system. More in particular, the insert in the direction of the flow of breathable gas first expands and then contracts to enclose the aerosol generator. This provides an insert with of relatively limited size. To accommodate the aerosol generator and in particular its connections the expanding part preferably comprises an open space.

In an arrangement, the aerosol generator is a nebulizer, more in particular a vibrating mesh nebulizer. Nebulizers are known and widely used to provide aerosols or aerosolized drugs. These are relatively silent, portable and small. Mesh nebulizers are particularly advantageous to nebulize or aerosolize aqueous solutions.

In another arrangement, the system further comprises a control unit to control at least the ventilator and the aerosol generator, wherein in the control unit is configured to control the amount and humidity of the breathable gas based on a patient's needs. This enhances the flexibility and allows a better patient comfort.

BRIEF DESCRIPTION OF THE DRAWINGS

Examples of the invention will now be described in detail with reference to the accompanying drawings, in which.

DETAILED DESCRIPTION OF EMBODIMENTS

Figure 1:
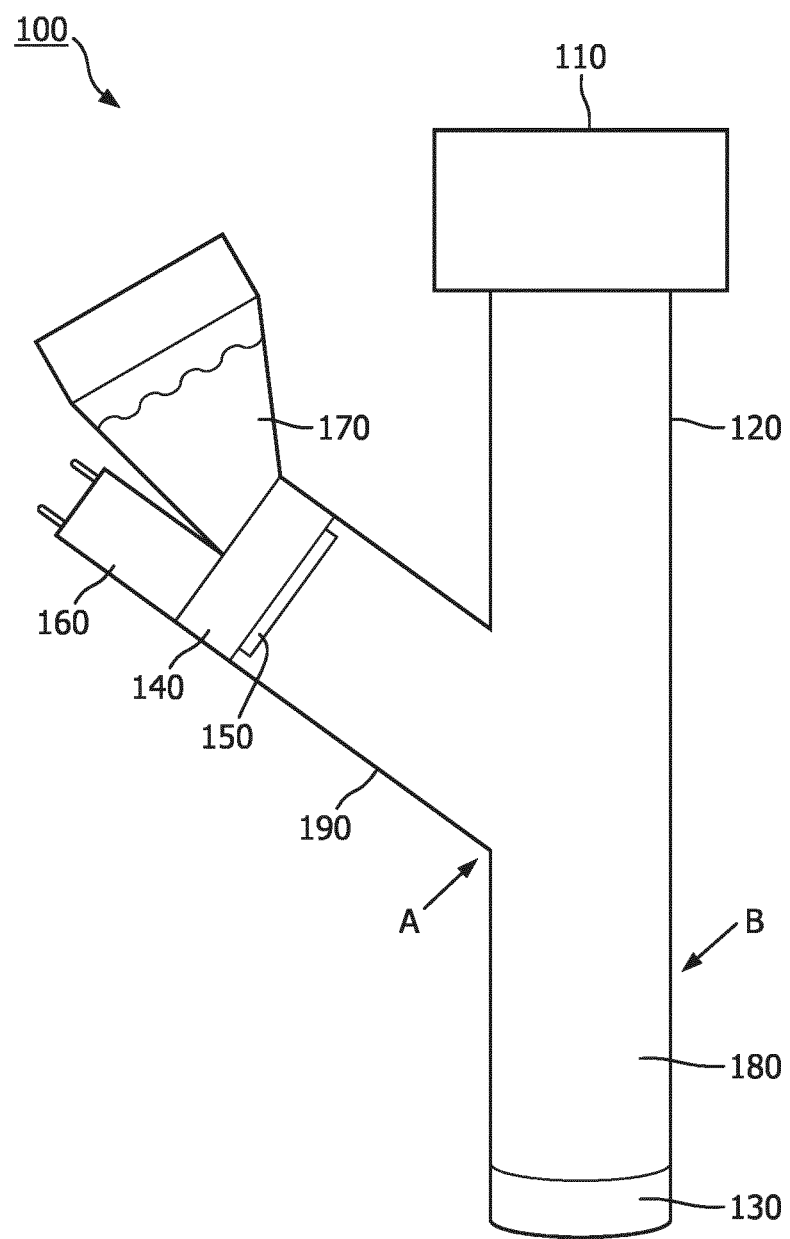
FIG. 1 shows a schematic view of a known system for humidification of a pressurized flow of breathable gas delivered to a patient.
Figure 2:
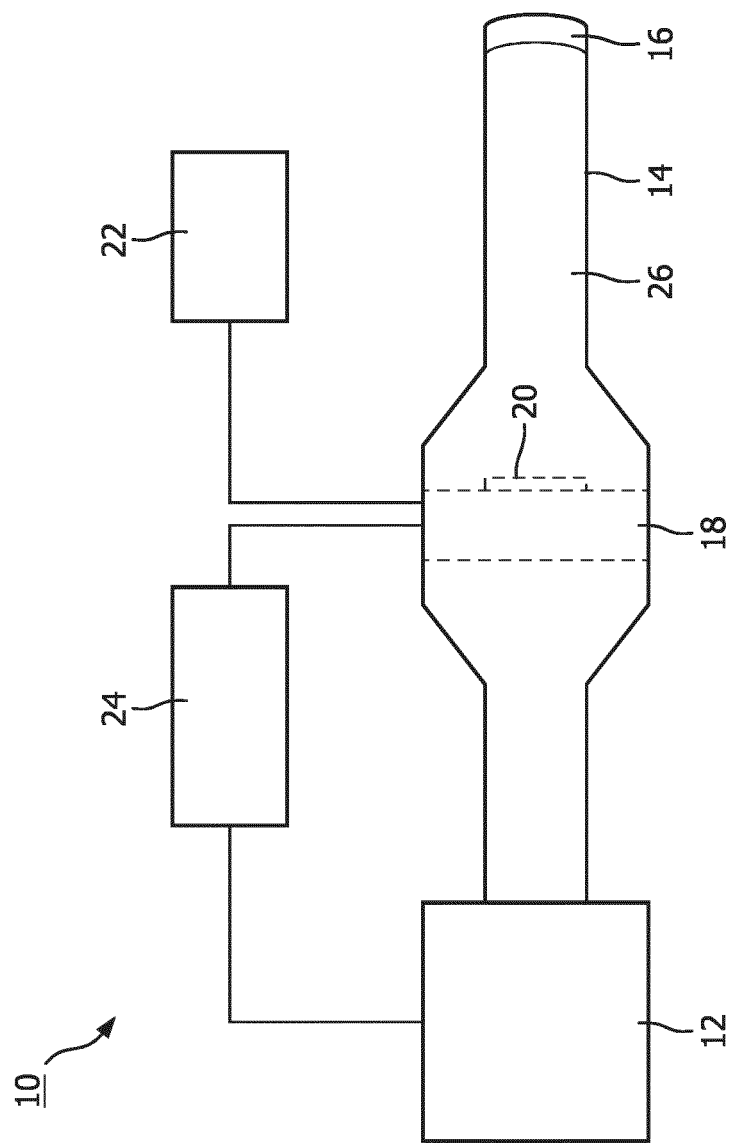
FIG. 2 shows a schematic view of a system for humidification of a pressurized flow of breathable gas delivered to a patient according to the invention.
Figure 3:
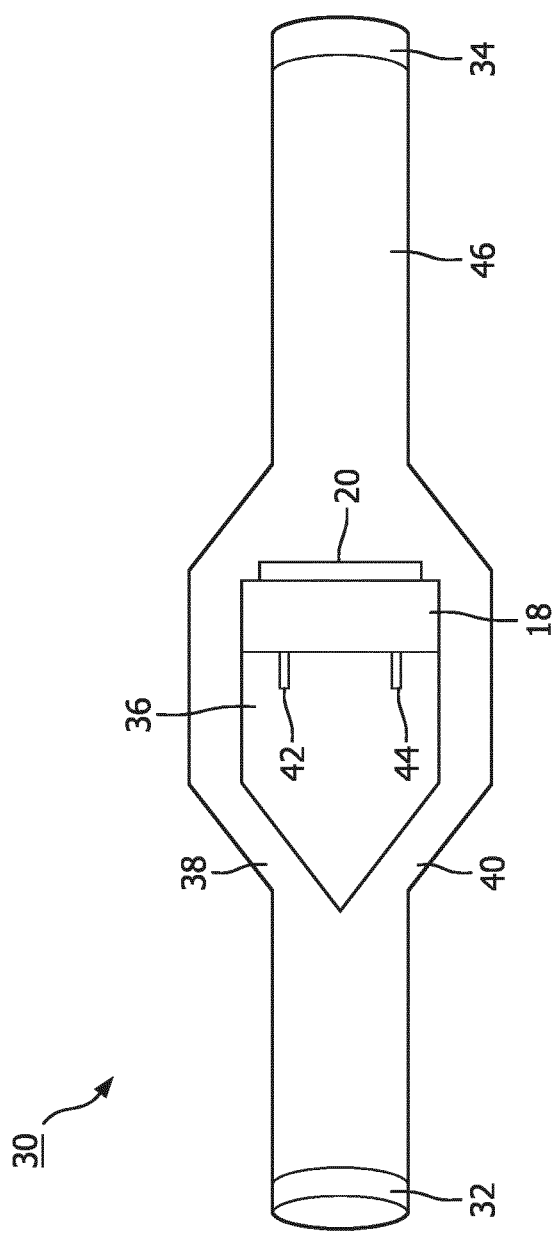
FIG. 3 shows a schematics view of an insert that is used in a system for humidification of a pressurized flow of breathable gas delivered to a patient as shown in FIG. 2.

As noted above, FIG. 1 shows a schematic view of a known system 100 for humidification of a pressurized flow of breathable gas delivered to a patient. The system 100 comprises a ventilator 110, a patient circuit 120 in fluid communication with the ventilator. The patient circuit has an internal space 180 for transportation of the breathable gas. At an end of the patient circuit a connector 130 is provided that is used to connect the patient circuit with the respiratory system of a patient. The system 100 further comprises an aerosol generator 140 having an outflow opening 150. The aerosol generator is connected to a liquid reservoir 170. A connection unit 160 is provided for the (electrical) connections of the aerosol generator. A connector 190 is provided to connect the outflow opening 150 of the aerosol generator with the patient circuit 120. At the locations indicated with arrows A and B there is a high risk for condensation to occur due to the collision of the small water droplets. Further on, the water droplets are created in a kind of dead volume that is not effectively flushed by the air delivered by the ventilator 110 towards the patient circuit connector 130. Therefore, the amount of droplets delivered to the patient per time unit is not well defined.

As noted above, FIG. 2 shows a schematic view of a system 10 for humidification of a pressurized flow of breathable gas delivered to a patient according to the invention. The system 10 comprises a ventilator 12, a patient circuit 14 in fluid communication with the ventilator. At and end of the patient circuit a connector 16 is provided that is used to connect the patient circuit with the respiratory system of a patient. The patient circuit has an internal space 26 for transportation of the breathable gas. The system further comprises an aerosol generator 18 having an outflow opening 20, both indicated with dotted lines. The outflow opening 20 is provided within the internal space 26 allowing a direct entrainment of the aerosol of liquid with the breathable gas.

Preferably the ventilator uses a turbine to generate the air flow towards the patient.

The system further comprises a control unit 24 that is connected to the ventilator 12 and the aerosol generator 18. The control unit preferably is configured to control the amount and humidity of the breathable gas based on a patient' needs. The control unit preferably arranges for the system to work only during (part of) the inhalation phase of the breathing cycle of a patient. Information on the breathing cycle to trigger on can be got, from the ventilator settings in case a ventilator that measures the breath rate is used.

The aerosol generator 18 is connected to a liquid reservoir 22.

As noted above, FIG. 3 shows a shows a schematic view of an insert 30 that is used in a system for humidification of a pressurized flow of breathable gas delivered to a patient as shown in FIG. 2. The insert at both ends comprises connectors 32 and 34 for easy connecting with or mounting to a patient (air) circuit. The flow direction of breathable gas runs from connector 32 at the left side to the connector 34 at the right side of the dawing. In this direction the insert first expands and then contracts. In this way space is made available to accommodate the aerosol generator 18. More particular the air tube first bifurcates into 2 separate parts 38 and 40 and then rejoins into a single part. The outflow opening 20 of the aerosol generator 18 debouches in the internal space 46 of the insert. The insert further comprises an open space 36 provided in the expanding part this allows the space for mounting of the aerosol generator 18. The aerosol generator 18 is mounted in the open space, 36, wherein the outflow opening 20 coincides with an opening in the outer wall of the insert 30. It also provides space for an electrical connection 42 and a connection to the liquid water reservoir 44 of the aerosol generator.

The aerosol generator ideally is placed as close to the patient as possible to avoid water losses in the circuit. The present invention enables such placement of due to the advantageous connection between the patient circuit and the aerosol generator.

Sterile water or sterile normal saline preferably is used as humidifying agent. Preferably the system is sealed from the atmosphere to reduce contamination risks. The breathable gas preferably is regular air.

Connection to the respiratory system of a patient can be obtained in a number of ways, for example one can connect the insert to an endrotracheal tube for intubated patients. Other possibilities are connection via a nasal of facial mask. It is also possible to use the system in combination with a device delivering a positive pressure (CPAP-) for treating sleep apnea.

The system can be advantageously used for a whole range of patients that have breathing difficulties with their respiratory system, such as chronic obstructive pulmonary disease (COPD) patients, asthma patients or patients with neuromuscular disorders.

Experiments have been performed to demonstrate the improvement of the design as shown in FIGS. 2 and 3 in comparison with the design shown in FIG. 1. The patient respiratory system was replaced by an artificial lung with a volume of 0.6 litre. The peak flow of the ventilator (during inhalation phase) was set at 70 L/min and a breathing cycle with 1 s for inhalation and with 2 s for exhalation was used. Further an amount of up to 33 mg of water per liter air generated by the nebulizer was used. It was found that the system according to the invention shows proper mixing of air with the water droplets and no rainout. Running the known system under same conditions resulted in worse mixing of air and water and rainout that is clearly visible in the regions indicated with arrows A and B of the known system as shown in FIG. 1.

During operation of the system a power of <~2 W is consumed. The existing active humidification devices wherein humidifaction is based on heating of water need more than an order of magnitude higher power. The relative low power consumption and the efficient design for example in terms of relative size—allows for a system that is battery operated and portable. Portable systems of course greatly enhance the comfort and flexibility of a patient.

The present invention provides a system for humidification of a pressurized flow of breathable gas delivered to a patient, the system comprising; a ventilator for generating a pressurized flow of breathable gas; a patient circuit in fluid communication with the ventilator and connectable to the respiratory system of a patient; and an aerosol generator. The patient circuit defines an internal space for transporting the flow of breathable gas which internal space accommodates the outflow opening of the aerosol generator. This enables to prevent so-called rainout and a relatively light weight portable system. The invention also relates to an insert that is connectable to the patient circuit and that accommodates the aerosol generator.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for humidification of a pressurized flow of breathable gas delivered to a patient, the system comprising:

a ventilator for generating a pressurized flow of breathable gas;

a patient circuit in fluid communication with the ventilator and connectable to the respiratory system of a patient, the patient circuit defining an internal space for transportation of the breathable gas;

an insert that is connectable to the patient circuit to form part thereof;

an aerosol generator for providing an aerosol of liquid, the aerosol generator having an outflow opening;

wherein the insert comprises an air tube that, in the direction of the flow of breathable gas, first bifurcates into two separate parts, thereby defining an open space external to the air tube that accommodates the aerosol generator, and then rejoins into a single part;

wherein the outflow opening is provided within the internal space for entrainment of the aerosol of liquid; and wherein the outflow opening coincides with an opening in an outer wall of the air tube of the insert.

2. The system according to claim 1, wherein the insert in the direction of the flow of breathable gas first expands and then contracts to enclose the outflow opening of the aerosol generator.

3. The system according to claim 1, wherein the aerosol generator is connected to a liquid reservoir via the open space.

4. The system according to claim 1, wherein the aerosol generator is a nebulizer.

5. The system according to claim 1, wherein the system further comprises a control unit electrically connected to at least the ventilator and the aerosol generator, wherein the control unit is configured to control the amount and humidity of the breathable gas based on a patient's needs.

6. The system according to claim 1, wherein the system is a battery operated portable system.

7. The system of claim 1, wherein the air tube bifurcates into two separate parts, each defining a passageway around the aerosol generator, and then rejoining into the single part.

8. The system of claim 7, wherein the air tube comprises a y-shaped element that bifurcates the air tube into each respective passageway.

9. The system of claim 1, comprising one or more of a controller and a liquid reservoir, each being located external to the open space;

wherein:

the open space of the air tube is configured to accommodate one or more connections of the aerosol generator; and the one or more connections include one or more of an electrical connection for the controller and a connection for the liquid reservoir.

10. The system of claim 9, whereby the one or more of an electrical connection for the controller and a connection for the liquid reservoir transit via the open space and do not connect via passageways of the air tube.

11. An insert comprising:

one or more connections configured to connect to a patient circuit of a ventilator system to form a part thereof; and an aerosol generator configured to provide an aerosol of liquid, the aerosol generator having an outflow opening;

wherein the insert comprises an air tube that, in the direction of flow of breathable gas, first bifurcates into two separate parts, thereby defining an open space external to the air tube that accommodates the aerosol generator, and then rejoins into a single part;

wherein the outflow opening is provided within an internal space of the patient circuit for entrainment of the aerosol of liquid; and wherein the outflow opening coincides with an opening in an outer wall of the air tube of the insert.

12. The insert of claim 11, wherein the aerosol generator comprises one or more connections accessible via the open space.

13. The insert of claim 12, wherein the one or more connections include one or more of an electrical connection and a liquid reservoir connection.

14. The insert of claim 13, wherein the electrical connection operatively couples the aerosol generator to a control unit.

15. An insert, comprising:

one or more connections configured to connect to a patient circuit of a ventilator system to form a part thereof; and an air tube that, in the direction of flow of breathable gas, first bifurcates into two separate parts, thereby defining an open space external to the air tube, and then rejoins into a single part;

wherein the open space is configured to accommodate an aerosol generator that, in a state where the insert is connected to form part of the patient circuit, occupies at least part of the open space and has an aerosol outflow positioned into the flow of breathable gas directed towards a patient; and wherein the outflow opening coincides with an opening in an outer wall of the air tube of the insert.

16. The insert of claim 15, wherein the open space of the air tube is configured to accommodate one or more connections of the aerosol generator.

17. The insert of claim 16, wherein the one or more connections include one or more of an electrical connection and a liquid reservoir connection.

* * * * *